| (12) | United States Patent | (10) Patent No.: | US 8,067,089 B2 |
|---|---|---|---|
| | Schwantes | (45) Date of Patent: | *Nov. 29, 2011 |

(54) CATIONIC MICROCAPSULE PARTICLES

(75) Inventor: Todd Arlin Schwantes, Lena, WI (US)

(73) Assignee: Appleton Papers Inc., Appleton, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/382,946

(22) Filed: Mar. 27, 2009

(65) Prior Publication Data

US 2009/0274905 A1 Nov. 5, 2009

Related U.S. Application Data

(63) Continuation-in-part of application No. 12/149,424, filed on May 1, 2008, which is a continuation-in-part of application No. 12/221,781, filed on Aug. 6, 2008.

(51) Int. Cl.
*B32B 27/14* (2006.01)

(52) U.S. Cl. ........... 428/402.2; 428/402.21; 428/402.22; 427/213.3

(58) Field of Classification Search ............... 428/402; 424/401; 402/21, 22; 526/319, 73, 310, 526/312

See application file for complete search history.

(56) References Cited

U.S. PATENT DOCUMENTS

| 2,730,456 A | 1/1956 | Greene et al. ................. 503/214 |
|---|---|---|
| 2,800,457 A | 7/1957 | Greene et al. ............... 428/402.2 |
| 2,800,458 A | 7/1957 | Greene et al. ............... 428/402.2 |
| 3,516,941 A | 6/1970 | Matson ........................ 264/4.33 |
| 3,660,304 A | 5/1972 | Matsukawa .................... 264/4.3 |
| 3,886,085 A | 5/1975 | Kiritani et al. ............. 428/402.21 |
| 3,965,033 A | 6/1976 | Matsukawa et al. ........... 264/4.3 |
| 4,001,140 A | 1/1977 | Foris et al. ..................... 252/316 |

(Continued)

FOREIGN PATENT DOCUMENTS

EP 1 637 188 A1 8/1920

(Continued)

OTHER PUBLICATIONS

"Microencapsulation" in Kirk-Othmer Encyclopedia of Chemical Technology, Fifth Edition, pp. 438-463.

(Continued)

*Primary Examiner* — James J Seidleck
*Assistant Examiner* — S. Camilla Pourbohloul
(74) *Attorney, Agent, or Firm* — Benjamin Mieliulis (57) ABSTRACT

The present invention teaches a cationically charged or neutral microcapsule particle comprising an oil soluble or dispersible core material and a wall material at least partially surrounding the core material, the microcapsule wall material comprising the reaction product of a first composition in the presence of a second composition comprising an emulsifier which is cationic or nonionic, the first composition comprising a reaction product of i) an oil soluble or dispersible amine with ii) a multifunctional acrylate or methacrylate monomer or oligomer, an oil soluble acid and an initiator. The cationic or nonionic emulsifier comprises a water soluble or water dispersible material and optionally a water phase initiator. The first composition initiator and the water phase initiator is an energy-activated initiator. The reaction product of the first composition and second composition results in the formation of a population of microcapsules having a microcapsule wall of low permeance to the core material and having a zeta potential of −5 millivolts or greater. The resulting microcapsules have adherence to anionic surfaces.

25 Claims, 1 Drawing Sheet

U.S. PATENT DOCUMENTS

| | | |
|---|---|---|
| 4,075,134 A | 2/1978 | Morehouse, Jr. .............. 524/460 |
| 4,087,376 A | 5/1978 | Foris et al. .................... 252/316 |
| 4,089,802 A | 5/1978 | Foris et al. .................... 252/316 |
| 4,093,556 A | 6/1978 | Wojciak ........................ 252/316 |
| 4,100,103 A | 7/1978 | Foris et al. .................... 252/316 |
| 4,105,823 A | 8/1978 | Hasler et al. ................. 428/307 |
| 4,166,152 A | 8/1979 | Baker et al. ................... 428/522 |
| 4,197,346 A | 4/1980 | Stevens ......................... 428/307 |
| 4,221,710 A | 9/1980 | Hoshi et al. .................. 260/17.3 |
| 4,251,386 A | 2/1981 | Saeki et al. ................... 252/316 |
| 4,285,720 A | 8/1981 | Scher ................................ 71/88 |
| 4,356,109 A | 10/1982 | Saeki et al. ................... 252/316 |
| 4,444,699 A | 4/1984 | Hayford ......................... 264/4.7 |
| 4,547,429 A | 10/1985 | Greiner et al. ........... 428/402.24 |
| 4,552,811 A | 11/1985 | Brown et al. ............ 428/402.21 |
| 4,588,639 A | 5/1986 | Ozono ..................... 428/402.22 |
| 4,601,863 A | 7/1986 | Shioi et al. ..................... 264/4.3 |
| 4,610,927 A | 9/1986 | Irgarashi et al. ......... 428/402.21 |
| 4,622,267 A | 11/1986 | Riecke ..................... 428/402.21 |
| 4,708,924 A | 11/1987 | Nagai et al. ................... 430/138 |
| 4,908,271 A | 3/1990 | Kasai et al. .............. 428/402.22 |
| 5,105,823 A | 4/1992 | Hasler et al. ................. 128/754 |
| 5,126,061 A | 6/1992 | Michael ........................ 510/106 |
| 5,292,835 A | 3/1994 | Jahns et al. ...................... 526/73 |
| 5,407,609 A | 4/1995 | Tice et al. ......................... 264/46 |
| 5,596,051 A * | 1/1997 | Jahns et al. ...................... 526/73 |
| 6,375,872 B1 | 4/2002 | Chao ............................. 264/4.33 |
| 6,531,156 B1 | 3/2003 | Clark ............................. 424/489 |
| 6,592,990 B2 | 7/2003 | Schwantes ............... 428/402.21 |
| 2002/0068805 A1* | 6/2002 | Futami et al. .............. 526/307.5 |
| 2008/0317795 A1* | 12/2008 | Traynor et al. ............... 424/401 |

FOREIGN PATENT DOCUMENTS

| | | |
|---|---|---|
| EP | 0198089 | 10/1990 |
| FR | 2801811 B | 5/2002 |
| JP | 10-294293 | 10/1998 |
| JP | 2002-235483 | 8/2002 |
| WO | 01/41915 A1 | 6/2001 |
| WO | WO 01/41915 | 6/2001 |
| WO | 2006/127453 | 11/2006 |

OTHER PUBLICATIONS

"Capsular Adhesives" in The Journal of the Technical Association of the Pulp and Paper Industry, vol. 49, No. 5 May 1966 pp. 41A-44A.

* cited by examiner

Figure 1

CATIONIC MICROCAPSULE PARTICLES

This application is a continuation-in-part of Schwantes U.S. Ser. No. 12/149,424 filed May 1, 2008, pending, and U.S. Ser. No. 12/221,781 filed Aug. 6, 2008, pending.

FIELD OF THE INVENTION

This invention relates to capsule manufacturing processes and microcapsules produced by such processes.

DESCRIPTION OF THE RELATED ART

Various processes for microencapsulation, and exemplary methods and materials are set forth in Schwantes (U.S. Pat. No. 6,592,990), Nagai et. al. (U.S. Pat. No. 4,708,924), Baker et. al. (U.S. Pat. No. 4,166,152), Wojciak (U.S. Pat. No. 4,093,556), Matsukawa et. al. (U.S. Pat. No. 3,965,033), Matsukawa (U.S. Pat. No. 3,660,304), Ozono (U.S. Pat. No. 4,588,639), Irgarashi et. al. (U.S. Pat. No. 4,610,927), Brown et. al. (U.S. Pat. No. 4,552,811), Scher (U.S. Pat. No. 4,285,720), Shioi et. al. (U.S. Pat. No. 4,601,863), Kiritani et. al. (U.S. Pat. No. 3,886,085), Jahns et. al. (U.S. Pat. Nos. 5,596,051 and 5,292,835), Matson (U.S. Pat. No. 3,516,941), Chao (U.S. Pat. No. 6,375,872), Foris et. al. (U.S. Pat. Nos. 4,001,140; 4,087,376; 4,089,802 and 4,100,103), Greene et. al. (U.S. Pat. Nos. 2,800,458; 2,800,457 and 2,730,456), Clark (U.S. Pat. No. 6,531,156), Saeki et. al. (U.S. Pat. Nos. 4,251,386 and 4,356,109), Hoshi et. al. (U.S. Pat. No. 4,221,710), Hayford (U.S. Pat. No. 4,444,699), Hasler et. al. (U.S. Pat. No. 5,105,823), Stevens (U.S. Pat. No. 4,197,346), Riecke (U.S. Pat. No. 4,622,267), Greiner et. al. (U.S. Pat. No. 4,547,429), and Tice et. al. (U.S. Pat. No. 5,407,609), among others and as taught by Herbig in the chapter entitled "Microencapsulation" in Kirk-Othmer Encyclopedia of Chemical Technology, V.16, pages 438-463.

More particularly, U.S. Pat. Nos. 2,730,456; 2,800,457; and 2,800,458 describe methods for capsule formation. Other useful methods for microcapsule manufacture are: U.S. Pat. Nos. 4,001,140; 4,081,376 and 4,089,802 describing a reaction between urea and formaldehyde; U.S. Pat. No. 4,100,103 describing reaction between melamine and formaldehyde; British Pat. No. 2,062,570 describing a process for producing microcapsules having walls produced by polymerization of melamine and formaldehyde in the presence of a styrene-sulfonic acid. Forming microcapsules from urea-formaldehyde resin and/or melamine formaldehyde resin is disclosed in U.S. Pat. Nos. 4,001,140; 4,081,376, 4,089,802; 4,100,103; 4,105,823; and 4,444,699. Alkyl acrylate-acrylic acid copolymer capsules are taught in U.S. Pat. No. 4,552,811. Each patent described throughout this application is incorporated herein by reference to the extent each provides guidance regarding microencapsulation processes and materials.

Interfacial polymerization is a process wherein a microcapsule wall of a polyamide, an epoxy resin, a polyurethane, a polyurea or the like is formed at an interface between two phases. U.S. Pat. No. 4,622,267 discloses an interfacial polymerization technique for preparation of microcapsules. The core material is initially dissolved in a solvent and an aliphatic diisocyanate soluble in the solvent mixture is added. Subsequently, a nonsolvent for the aliphatic diisocyanate is added until the turbidity point is just barely reached. This organic phase is then emulsified in an aqueous solution, and a reactive amine is added to the aqueous phase. The amine diffuses to the interface, where it reacts with the diisocyanate to form polymeric polyurethane shells. A similar technique, used to encapsulate salts which are sparingly soluble in water in polyurethane shells, is disclosed in U.S. Pat. No. 4,547,429. U.S. Pat. No. 3,516,941 teaches polymerization reactions in which the material to be encapsulated, or core material, is dissolved in an organic, hydrophobic oil phase which is dispersed in an aqueous phase. The aqueous phase has dissolved materials forming aminoplast resin which upon polymerization form the wall of the microcapsule. A dispersion of fine oil droplets is prepared using high shear agitation. Addition of an acid catalyst initiates the polycondensation forming the aminoplast resin within the aqueous phase, resulting in the formation of an aminoplast polymer which is insoluble in both phases. As the polymerization advances, the aminoplast polymer separates from the aqueous phase and deposits on the surface of the dispersed droplets of the oil phase to form a capsule wall at the interface of the two phases, thus encapsulating the core material. This process produces the microcapsules. Polymerizations that involve amines and aldehydes are known as aminoplast encapsulations. Urea-formaldehyde (UF), urea-resorcinol-formaldehyde (URF), urea-melamine-formaldehyde (UMF), and melamine-formaldehyde (MF), capsule formations proceed in a like manner. In interfacial polymerization, the materials to form the capsule wall are in separate phases, one in an aqueous phase and the other in a fill phase. Polymerization occurs at the phase boundary. Thus, a polymeric capsule shell wall forms at the interface of the two phases thereby encapsulating the core material. Wall formation of polyester, polyamide, and polyurea capsules typically proceeds via interfacial polymerization.

U.S. Pat. No. 5,292,835 teaches polymerizing esters of acrylic acid or methacrylic acid with polyfunctional monomers. Specifically illustrated are reactions of polyvinylpyrrolidone with acrylates such as butanediol diacrylate or methylmethacrylate together with a free radical initiator.

Common microencapsulation processes can be viewed as a series of steps. First, the core material which is to be encapsulated is typically emulsified or dispersed in a suitable dispersion medium. This medium is typically aqueous but involves the formation of a polymer rich phase. Most frequently, this medium is a solution of the intended capsule wall material. The solvent characteristics of the medium are changed such as to cause phase separation of the wall material. The wall material is thereby contained in a liquid phase which is also dispersed in the same medium as the intended capsule core material. The liquid wall material phase deposits itself as a continuous coating about the dispersed droplets of the internal phase or capsule core material. The wall material is then solidified. This process is commonly known as coacervation.

The capsules according to the invention are useful with a wide variety of capsule contents ("core materials") including, by way of illustration and without limitation, internal phase oils, solvent oils, phase change materials, dyes, perfumes, fragrances, cleaning oils, polishing oils, flavorants, nutrients, sweeteners, chromogens, pharmaceuticals, fertilizers, herbicides, biological actives, scents, and the like. The microcapsule core materials can include materials which alter rheology or flow characteristics, or extend shelf life or product stability. Essential oils as core materials can include, for example, by way of illustration wintergreen oil, cinnamon oil, clove oil, lemon oil, lime oil, orange oil, peppermint oil and the like. Dyes can include fluorans, lactones, indolyl red, I6B, leuco dyes, all by way of illustration and not limitation. The core material should be dispersible or sufficiently soluble in the capsule internal phase material namely in the internal phase oil or soluble or dispersible in the monomers or oligomers solubilized or dispersed in the internal phase oil. The core materials are preferably liquid but can be solid depending on the materials selected, and with temperatures appropriately adjusted to effect dispersion.

U.S. Pat. No. 4,046,750 teaches an ionene modified polymeric bead. Dimethylamino substituted acrylic polymer is cross-linked and then the formed beads are reacted with a mixture of ditertiary amine and a dihalide to attach ionene segments to the tertiary amine centers on the beads. Insoluble cationic modified beads are formed. These cationic beads are useful in affinity chromatography.

Microcapsule Technologies in WO 01/41915 teaches coating formed anionic microcapsules by adding compounds with a cationic charge in a controlled manner. For example polyurea capsules are introduced to a solution of vinylpyrrolidone to coat the capsules and render them with cationic character. Similarly melamine microcapsules are taught to be coated with a homogenous solution of hydroxypropyl guar to impact cationic character. Gelatin capsules are illustrated coated with hydroxyethyl cellulose followed by epichlorhydrin to render them cationic.

Firmenich in EP 1637188 describes flowable dispersions of coacervate capsules based on acrylamido methylpropane sulfonate with a thickening polymer of nonionic and cationic polymers. A complex between the anionic aminoplast capsules and cationic polymer is though beneficial to drive the deposition of the capsules from rinse off formulations onto surfaces to which the capsules are applied.

Similar to the approach of Microcapsule Technologies, U.S. publication 2005/0112152 also teaches applying a second coating of a cationic material over an acrylamide and melamine formaldehyde based wall. Cationic polymer coated capsules are taught prepared by mixing uncoated fragrance containing capsules with a cationic polymeric deposition aid.

Each of the above methods is deficient to form cationic microcapsules of low permance and/or rely on multiple layers making the processes unattractive commercially.

The capsules of the present invention are the reaction product of an amine with acrylate along with a soluble acid and an initiator. Reaction is carried out in the presence of a cationic or nonionic emulsifier. The resultant capsule wall material exhibits a zeta potential of −5.0 millivolts or greater. The resulting capsules have low permeability and strong adherence to anionic surfaces.

The capsules are useful to deliver a desired core material and to adhere it to surfaces such as textiles, and anionic substrates.

Although encapsulation of various materials is known in the art, a need exists for capsules and particles which adhere to various surfaces. A need also exists for low permeability microcapsules which are cationic or non-ionic and which adhere especially to anionic surfaces. These and other embodiments are set forth in the invention specification herein.

SUMMARY OF THE INVENTION

The present invention discloses a population of microcapsule particles comprising an oil soluble or dispersible core material and a wall material at least partially surrounding the core material. The microcapsule wall material comprises the reaction product of a first composition in the presence of a second composition comprising an emulsifier which is cationic or nonionic. The first composition comprises a reaction product selected from the group consisting of A) a reaction product of i) an oil soluble or dispersible amine acrylate or methacrylate with ii) a multifunctional acrylate or methacrylate monomer or oligomer, and iii) an oil-soluble acid and an initiator, B) a reaction product of i) an oil soluble or dispersible acid acrylate or methacrylate with ii) a multifunctional acrylate or methacrylate monomer or oligomer, and iii) a oil-soluble base and an initiator, C) a reaction product of i) an oil-soluble or dispersible amine acrylate or methacrylate with ii) a multifunctional acrylate or methacrylate monomer or oligomer, and iii) a water-soluble acid and an initiator, and D) a reaction product of i) an oil-soluble or dispersible acid acrylate or methacrylate with ii) a multifunctional acrylate or methacrylate monomer or oligomer, and iii) a water-soluble base and an initiator.

The cationic or nonionic emulsifier comprises a water-soluble or water-dispersible material and optionally a warm phase initiator, where the first composition initiator and the water phase initiator is an energy-activated initiator. The reaction product of the first composition and second composition results in the formation of a population of microcapsules having a microcapsule wall of low permeance to the core material and having a zeta potential of −5 millivolts or greater, the resulting microcapsules having strong adherence to anionic surfaces.

DETAILED DESCRIPTION

Figure 1:
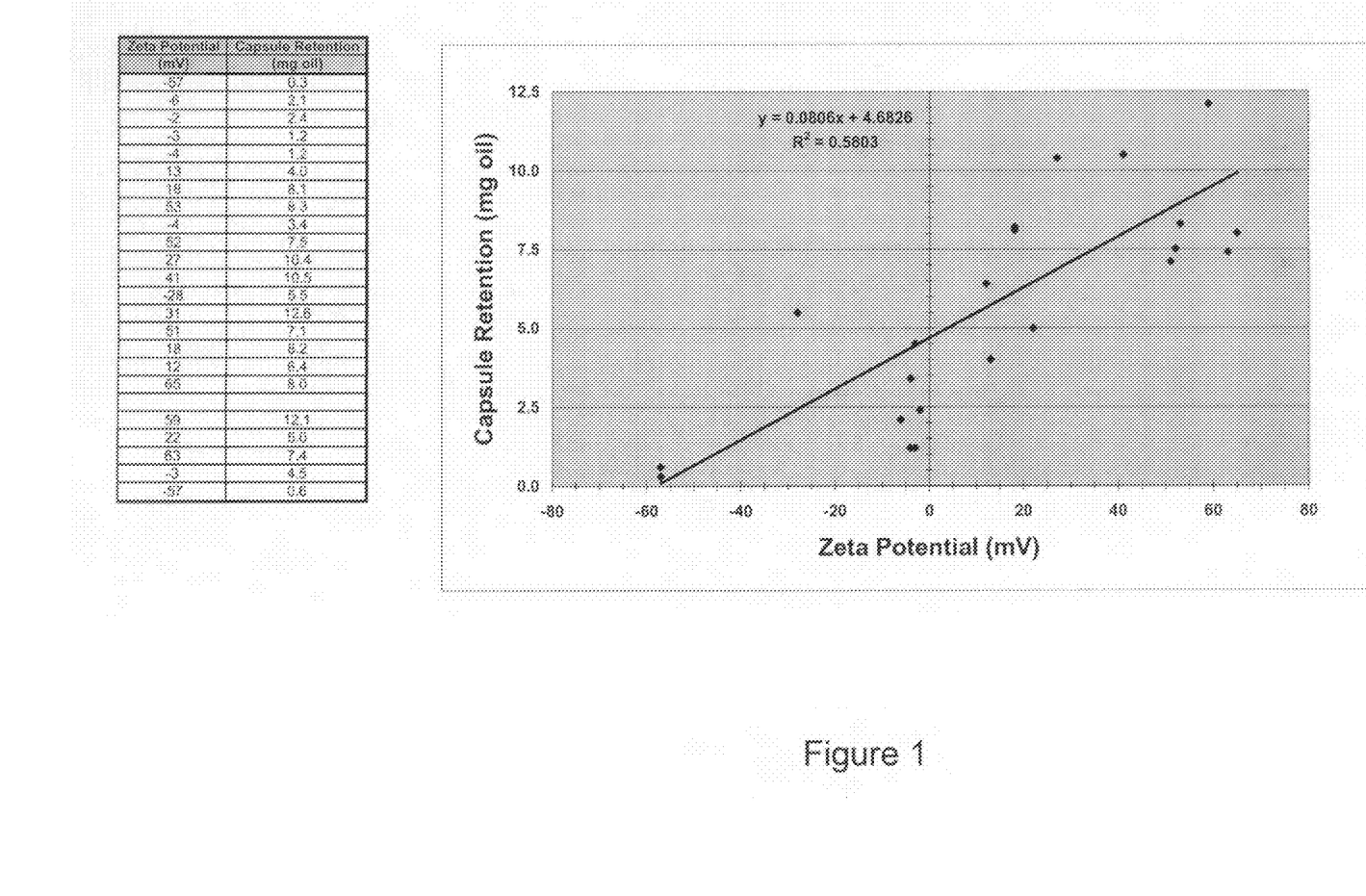
FIG. 1 is a graph of Zeta Potential versus capsule retention.

The present invention teaches a cationically charged or neutral microcapsule particle comprising an oil soluble or dispersible core material and a wall material at least partially surrounding the core material, the microcapsule wall material comprising the reaction product of a first composition in the presence of a second composition comprising an emulsifier which is cationic or nonionic, the first composition comprising a reaction product selected from the group consisting of A) a reaction product of i) an oil-soluble or dispersible amine acrylate or methacrylate with ii) a multifunctional acrylate or methacrylate monomer or oligomer, and iii) an oil-soluble acid and an initiator, B) a reaction product of i) an oil soluble or dispersible acid acrylate or methacrylate with ii) a multifunctional acrylate or methacrylate monomer or oligomer, and iii) an oil-soluble base and an initiator, C) a reaction product of i) an oil-soluble or dispersible amine acrylate or methacrylate with ii) a multifunctional acrylate or methacrylate monomer or oligomer, and iii) a water-soluble acid and an initiator, and D) a reaction product of i) an oil-soluble or dispersible acid acrylate or methacrylate with ii) a multifunctional acrylate or methacrylate monomer or oligomer, and iii) a water-soluble base and an initiator.

The cationic or nonionic emulsifier comprises a water soluble or water dispersible material and optionally a water phase initiator. The first composition initiator and the water phase initiator is an energy-activated initiator. The reaction product of the first composition and second composition results in the formation of a population of microcapsules having a microcapsule wall of low permeance to the core material and having a zeta potential of −5 millivolts or greater. The resulting microcapsules have adherence to anionic surfaces.

The emulsifier generally has a molecular weight greater than about 100. Cationic emulsifiers include amine polymers with primary, secondary or tertiary functionality. Nonionic emulsifiers can include polymers with hydroxyl, ether, esther, ketone and amide functionality.

Preferably the emulsifier is cationic. Preferably the cationic emulsifier is selected from palmitamidopropyltrimonium chloride, distearyl dimonium chloride, cetyltrimethylammonium chloride, quaternary ammonium compounds, fatty amines, aliphatic ammonium halides, alkyldimethylbenzylammonium halides, alkyldimethylethylammonium halides, polyethyleneimine, poly(2-dimethylamino)ethyl methacrylate)methyl chloride quaternary salt, poly(1-vinylpyrrolidone-co-2-dimethylaminoethyl methacrylate), poly(acrylamide-co-diallyldimethylammonium chloride), poly(allylamine), poly[bis(2-chloroethyl)ether-alt-1,3-bis[3-(dimethylamino)propyl]urea] quaternized, and poly(dimethylamine-co-epichlorohydrin-co-ethylenediamine), and condensation products of aliphatic amines with alkylene oxide.

In an alternative embodiment the emulsifier is nonionic. Preferably the nonionic emulsifier is selected from polyalkylene glycol ether, condensation products of alkyl phenols, aliphatic alcohols, or fatty acids with alkylene oxide, ethoxylated alkyl phenols, ethoxylated arylphenols, ethoxylated polyaryl phenols, carboxylic esters solubilized with a polyol, polyvinyl alcohol, polyvinyl acetate, or copolymers of polyvinyl alcohol polyvinyl acetate, polyacrylamide, poly(N-isopropylacrylamide), poly(2-hydroxypropyl methacrylate), poly(2-ethyl-2-oxazoline), poly(2-isopropenyl-2-oxazoline-co-methyl methacrylate), poly(methyl vinyl ether), and polyvinyl alcohol-co-ethylene). Especially useful polyvinylalcohols include polyvinyl alcohols of molecular weight 13000 to 186000 daltons, preferably from 13000 to about 23000 daltons, or even from 146000 to 186000 daltons. The polyvinyl alcohol can be partially or fully hydrolyzed.

Polyvinyl alcohol partially hydrolyzed in the range of 85 to 95% hydrolyzed is preferred. Partially hydrolyzed polyvinylalcohol at 88% hydrolysis or less was useful, with about 88% hydrolysis being more preferred.

Preferably the cationic emulsifier is polyalkylenimine compound wherein the alkylene moieties are from 2 and 8 carbons. Preferred is poly(ethyleneimine) of molecular weight from 1000 to about 250000.

Useful amines can include by way of illustration and not limitation amine modified vinyl monomers including amine modified acrylates or methacrylates such as mono or diacrylate amines, mono or dimethacrylate amines, amine modified polyetheracrylates and amine modified polyethermethacrylates, aminoalkyl acrylates or aminoalkyl methacrylate.

The amines can include primary, secondary or tertiary amines and can include tertiary butyl aminethylmethacrylate, diethylaminoethyl methacrylate, or dimethylaminoethyl methacrylate. Water soluble bases preferably include typical bases such as NaOH or KOH, but can also include other typical oxides and hydroxides of metals and ammonia.

Multifunctional acrylate or methacrylate monomers or oligomers can include mono-; di-; tri-; tetra- penta-; hexa-; hepta-; or octa-functional acrylate esters, methacrylate esters and multi-functional polyurethane acrylate esters and epoxy acrylates stable in the presence of initiator. Monomers shall be understood as including oligomers thereof. Optionally, an inhibitor such as hydroquinone can be added to the monomer and initiator blend in the capsules to prevent premature polymerization.

Useful monomers in the invention are di- and poly-functional acrylate esters, difunctional (meth)acrylate esters, polyfunctional (meth)acrylate esters, difunctional urethane acrylate esters, polyfunctional urethane acrylate esters and polyfunctional and difunctional epoxy acrylate monomers and oligomers used alone or in combination as blends. In alternate embodiments, optionally, the di- and polyfunctional acrylates, methacrylates, urethane acrylates, and epoxy acrylates are further blended with monofunctional acrylates, methacrylates, urethane acrylates and epoxy acrylates.

In an aspect of the invention multi-functional acrylate or methacrylate monomers or oligomers preferably are selected to have a Tg>60° C. in one aspect greater than 70° C., and in another aspect greater than 80° C., and can include by way of illustration and not limitation, allyl methacrylate; triethylene glycol dimethacrylate; ethylene glycol dimethacrylate, diethylene glycol dimethacrylate, aliphatic or aromatic urethane diacrylates, difunctional urethane acrylates, ethoxylated aliphatic difunctional urethane methacrylates, aliphatic or aromatic urethane dimethacrylates, epoxy acrylates, epoxymethacrylates; tetraethylene glycol dimethacrylate; polyethylene glycol dimethacrylate; 1,3 butylene glycol diacrylate; 1,4-butanediol dimethacrylate; 1,4-butaneidiol diacrylate; diethylene glycol diacrylate; 1,6 hexanediol diacrylate; 1,6 hexanediol dimethacrylate; neopentyl glycol diacrylate; polyethylene glycol diacrylate; tetraethylene glycol diacrylate; triethylene glycol diacrylate; 1,3 butylene glycol dimethacrylate; tripropylene glycol diacrylate; ethoxylated bisphenol diacrylate; ethoxylated bisphenol dimethylacrylate; dipropylene glycol diacrylate; alkoxylated hexanediol diacrylate; alkoxylated cyclohexane dimethanol diacrylate; propoxylated neopentyl glycol diacrylate, trimethylolpropane trimethacrylate; trimethylolpropane triacrylate, pentaerythritol triacrylate, ethoxylated trimethylolpropane triacrylate, propoxylated trimethylolpropane triacrylate, propoxylated glyceryl triacrylate, ditrimethylolpropane tetraacrylate, dipentaerythritol pentaacrylate, ethoxylated pentaerythritol tetraacrylate.

The oil soluble acid is preferably an organic acid. The organic acid can be selected from various acids such as carboxy acids, with monoalkyl maleates such as monomethyl, monoethyl or monobutyl maleate being preferred, with monobutyl maleate being most preferred. Other preferred organic acids include beta-carboxyethyl acrylate. Yet other organic acids that can be usefully employed in the invention include, organic sulfonic acids such as alkyl benezene sulfonic acid, more particularly linear alkyl benzene sulfonic acid, tridecylbenzene sulfonic acid, more particularly linear trialkyl benzene sulfonic acid such as linear tridecyl benzene sulfonic acid, alkyldiphenyloxide sulfonic acid, preferably dodecyl diphenyl oxidedisulfonic acid, more particularly branched C12 diphenyl oxide disulfonic acid, alkylbenzene sulfonic acid, more particularly, dodecyl benzene sulfonic acid, dialkyl naphthalene disulfonic acid, more particularly dinonyinaphthalene disulfonic acid, 4-hydrozino benzene sulfonic acid acrylic acid, methacrylic acid, and the like. Desirably the organic acid is selected to be dispersible in the oil phase and sparingly soluble in the water phase. The organic acid is used as 0.1 to 20%, preferably 3 to 10.0%, and more preferably 5.0-7.0% by weight based on percentage of total wall. Useful and preferred water soluble acids include standard strong acids such as HCl, $H_2SO_4$, and $H_3PO_4$. Acids are hydrogen ion source materials and can include mineral acids, solutions of hydrogen halides, and various materials that increase the concentration of hydrogen ions in solution.

Suitable emulsifiers for use herein are preferable cationic or nonionic emulsifiers. In certain circumstances amphoteric emulsifiers and zwitterionic emulsifiers can find applicability. Exemplary cationic emulsifiers include palmitamidopropyltrimonium chloride (Varisoft PATCH™, available from Degussa Evanik, Essen, Germany) distearyl dimonium chloride, cetyltrimethylammonium chloride, and polyethyleneimine.

The cationic emulsifiers include quaternary ammonium compounds with a long-chain aliphatic radical, e.g. distearyldiammonium chloride, and fatty amines. Among the cationic emulsifiers which may be mentioned are alkyldimethylbenzylammonium halides, alkyldimethylethylammonium halides, etc. Preferred emulsifiers are those which significantly reduce the interfacial tension between the aqueous phase and dispersed phase, and thereby reduce the tendency for droplet coalescence. Examples of nonionic emulsifiers include polyalkylene glycol ethers and condensation products of alkyl phenols, aliphatic alcohols, aliphatic amines or fatty acids with ethylene oxide, propylene oxide or mixtures of ethylene and propylene oxides such as the ethoxylated alkyl phenols or ethoxylated aryl or polyaryl phenols and carboxylic esters solubilized with a polyol, or polyvinyl alcohol(PVOH) or polyvinyl acetate or copolymers of PVOH/PVA. Amphoteric emulsifiers include alkylaminoalkanecarboxylic acids betaines, sulphobetaines, imidazoline derivatives, lauroamphoglycinate and sodium cocoaminopropionate. An exemplary zwitterionic emulsifier is cocoamidopropyl betaine. The amount of emulsifier is anywhere from about 0.1 to about 40 percent by weight of all constituents, more preferably from 0.5 to about 10 percent, most preferably 0.5 to 5 percent by weight. Typically emulsifier is employed at 0.2 to about 10% by weight based on percentage of the total formulation.

Excluding solvent, the primary, secondary or tertiary amine acrylate or methacrylate and the multi-functional acrylate or methacrylate monomers are used in a relative ratio of from about 0.1:99.9 to about 10:90 preferably from about 0.5:99.5 to about 5:95, and most preferably 1:99 to about 3:97.

For example, in the process of making the capsules, assuming a system of about 800 grams with solvent, the largest constituents are typically solvent, 10 to 70 weight percent, preferably 25 to 55 weight percent oil phase solvent and oil; 10 to 70 weight percent, preferably 35 to 65 weight percent water; 0.01 to 1 weight percent, preferably 0.025 to about 0.5 weight percent, more preferably 0.05 to 0.25% amine, preferably 0.1 to 10 weight percent, usually 0.5 to 8 weight percent multi-functional acrylate or methacrylate monomer or oligomer; oil to 20 weight percent. Initiator is 10% or less, usually about 5% or less, preferably 2% by weight or less and more preferably 1% or less. Low molecular weight secondary or tertiary amines can be also employed as the amine provided they are oil soluble or dispersible.

The initiators are energy activated meaning generating free radicals when subjected to heat or other energy input. Preferred initiators include peroxy initiators, azo initiators, peroxides, and compounds such as 2,2'-azobismethylbutyronitrile, dibenzoyl peroxide. More particularly, and without limitation the free radical initiator can be selected from the group of initiators comprising an azo or peroxy initiator, such as peroxide, dialkyl peroxide, alkyl peroxide, peroxyester, peroxycarbonate, peroxyketone and peroxydicarbonate, 2,2'-azobis(isobutylnitrile), 2,2'-azobis(2,4-dimethylpentanenitrile), 2,2'-azobis(2,4-dimethylvaleronitrile), 2,2'-azobis(2-methylpropanenitrile), 2,2'-azobis (methylbutyronitrile), 1,1'-azobis(cyclohexanecarbonitrile), 1,1'-azobis(cyanocyclohexane), benzoyl peroxide, decanoyl peroxide; lauroyl peroxide; benzoyl peroxide, di(n-propyl)peroxydicarbonate, di(sec-butyl)peroxydicarbonate, di(2-ethylhexyl) peroxydicarbonate, 1,1-dimethyl-3-hydroxybutyl peroxyneodecanoate, α-cumyl peroxyneoheptanoate, t-amyl peroxyneodecanoate, t-butyl peroxyneodecanoate, t-amyl peroxypivalate, t-butyl peroxypivalate, 2,5-dimethyl 2,5-di (2-ethylhexanoyl peroxy) hexane, t-amyl peroxy-2-ethylhexanoate, t-butyl peroxy-2-ethylhexanoate, t-butyl peroxyacetate, di-t-amyl peroxyacetate, t-butyl peroxide, di-t-amyl peroxide, 2,5-dimethyl-2,5-di-(t-butylperoxy)hexyne-3, cumene hydroperoxide, 1,1-di-(t-butylperoxy)-3,3,5-trimethyl-cyclohexane, 1,1-di-(t-butylperoxy)-cyclohexane, 1,1-di-(t-amylperoxy)-cyclohexane, ethyl-3,3-di-(t-butylperoxy)-butyrate, t-amyl perbenzoate, t-butyl perbenzoate, ethyl 3,3-di-(t-amylperoxy)-butyrate, and the like. Blends of initiators can also be employed. Initiators are available commercially, such as Vazo initiators, which typically indicate a decomposition temperature for the initiator. Preferably the initiator is selected to have a decomposition point of about 50° C. or higher. Usefully multiple initiators are employed, either as a blend in the oil phase, or in either of the oil or water phases. Preferably initiators are selected to stagger the decomposition temperatures at the various steps, pre-polymerization, wall formation and hardening or polymerizing of the capsule wall material. For example, a first initiator in the oil phase can decompose at 55° C., to promote prepolymer formation, a second can decompose at 60° C. to aid forming the wall material. Optionally a third initiator can decompose at 65° C. to facilitate polymerization of the capsule wall material. The total amount of initiator can be typically as low as 0.1 weight percent or as high as 10 weight percent.

Internal phase oils, or oil phase, or oil solvent or "nonsolvent for the water phase," used interchangeably for purposes hereof can be selected from solvents and the solvents can include by way of illustration and not limitation, ethyldiphenylmethane, butyl biphenyl ethane, benzylxylene, alkyl biphenyls such as propylbiphenyl and butylbiphenyl, dialkyl phthalates e.g. dibutyl phthalate, dioctylphthalate, dinonyl phthalate and ditridecylphthalate; 2,2,4trimethyl-1,3-pentanediol diisobutyrate, alkyl benzenes such as dodecyl benzene; alkyl or aralkyl benzoates such as benzyl benzoate; diaryl ethers, di(aralkyl)ethers and aryl aralkyl ethers, ethers such as diphenyl ether, dibenzyl ether and phenyl benzyl ether, liquid higher alkyl ketones (having at least 9 carbon atoms), alkyl or aralky benzoates, e.g., benzyl benzoate, alkylated naphthalenes such as dipropylnaphthalene, partially hydrogenated terphenyls; high-boiling straight or branched chain hydrocarbons, alkaryl hydrocarbons such as toluene, vegetable oils such as canola oil, soybean oil, corn oil, sunflower oil, or cottonseed oil, methyl esters of fatty acids derived from transesterification of canola oil, soybean oil, cottonseed oil, corn oil, sunflower oil, pine oil, lemon oil, olive oil, or methyl ester of oleic acid, vegetable oils, esters of vegetable oils, e.g. soybean methyl ester, straight chain saturated paraffinic aliphatic hydrocarbons of from 10 to 13 carbons. Mixtures of the above can also be employed. Common diluents such as straight chain hydrocarbons can also be blended with the solvents, or blend of solvents. The solvent is selected on the basis of hydrophobicity and ability to disperse or solvate the amine modified vinyl monomer and the multi-functional acrylate or methacrylate monomer or oligomer. "Internal phase oil" is herein to described as a type of oil material commonly able to be used as the oil in conventional microencapsulation. In conventional microencapsulation, the internal phase oil ends up as the core or internal contents of the microcapsule.

The microencapsulation process in certain of the embodiments is believed to rely on acid/base neutralization for formation of a charged species that drives the wall material to the oil/water interface. Charged species may also be formed through the use of an oil-soluble organic acidic acrylate or methacrylate with an inorganic water-soluble base, or an oil-soluble organic amine acrylate or methacrylate with an inorganic water-soluble base. Oil-soluble acids or bases may also be utilized, as appropriate, for neutralization of the acrylate or methacrylate acids or bases.

The size of the capsules can be controlled by adjusting the speed of agitation. Smaller size dispersions are achieved through faster agitation resulting in smaller capsules.

Emulsifying agents or protective colloids can be conveniently employed to facilitate dispersion. Such materials for example include cationic or non-ionic surfactants previously described.

The microcapsules according to the invention can be used to microencapsulate various core materials such as chromogens and dyes, flavorants, perfumes, sweeteners, fragrances, oils, fats, pigments, cleaning oils, pharmaceuticals, pharmaceutical oils, perfume oils, mold inhibitors, antimicrobial agents, adhesives, phase change materials, scents, fertilizers, nutrients, and herbicides by way of illustration and without limitation. The core can be liquid or even solid. With cores that are solid at ambient temperatures, the wall material can usefully enwrap less than the entire core for certain applications where availability of, for example, an agglomerate core is desired on application. Such uses can include scent release, cleaning compositions, emollients, cosmetic delivery and the like.

Microencapsulation can facilitate processing by increasing particle size or by converting liquids into free flowing solids. The largest volume applications of microcapsules are in imaging systems such as carbonless papers.

The microcapsule wall can serve the purpose of extending shelf life, stabilize and protect the core material, mask strong flavors, or protect contents so that they are available to participate in reactions such as imaging or adhesive formation when the capsule wall is ruptured, sheared, fractured, broken or melted.

The core material can be a minor or major constituent of the material encapsulated by the microcapsules. If the core material can function as the oil solvent in the capsules, it is possible to make the core material the major or total material encapsulated. Usually however, the core material is from 0.01 to 99 weight percent of the capsule internal contents, preferably 0.01 to about 65 by weight of the capsule internal contents, and more preferably from 0.1 to about 45% by weight of the capsule internal contents. With certain applications, the core can be effective even at just trace quantities.

In the process of the invention a first composition is prepared as an oil phase #1. The temperature of this oil phase is brought to a wall pre-reaction temperature. A nitrogen blanket is preferably employed and the solution mixed with high shear agitation to disperse the droplets. Gradually the temperature is increased to create a first composition reaction product.

A second oil phase is prepared and may be held at a pre-reaction temperature of the initiator.

The two oil solutions are allowed to pre-react and are combined. The mixtures are stirred and held at the pre-reaction temperature for sufficient time to pre-react the wall material. After the pre-reaction step, the water phase is added to the oil solutions.

The following is an illustration of preferred ranges with particular emulsifiers. Proportions are by weight.
For Cationic Capsule Type (Polyethyleneimine emulsifier):
Charged Materials (acid and base total quantity):
　Preferably: 0.1-20.0% by weight of total wall
　More Preferably: 0.5-10.0%
　Most Preferably: 1.0-5.0%
Acid/Base Molar proportions:
　Preferably: 3/1-1/3
　More Preferably: 2/1-1/2
　Most Preferably: 1.25/1-1/1.25
Water Phase pH:
　Preferably: 6-12
　More Preferably 7-11
　Most Preferably: 8-10
For Non-Ionic Capsule Type (Polyvinyl Alcohol emulsifier):
Charged Materials (acid and base total quantity):
　Preferably: 0.1-20.0% by weight of total wall
　More Preferably: 0.5-10.0%
　Most Preferably: 1.0-5.0%
Acid/Base Molar Proportions:
　Preferably: 3/1-1/3
　More Preferably: 2/1-1/2
　Most Preferably: 1.25/1-1/1.25
For Cationic Capsule Type (Polyethyleneimine emulsifier):
Charged Materials (acid and base total quantity):
　Preferably: 0.1-20.0% by weight of total wall
　More Preferably: 0.5-10.0%
　Most Preferably: 1.0-5.0%
Acid/Base Molar proportions:
　Preferably: 3/1-1/3
　More Preferably: 2/1-1/2
　Most Preferably: 1.25/1-1/1.25
Water Phase pH:
　Preferably: 6-12
　More Preferably 7-11
　Most Preferably: 8-10
For Non-Ionic Capsule Type (Polyvinyl Alcohol emulsifier):
Charged Materials (acid and base total quantity):
　Preferably: 0.1-20.0% by weight of total wall
　More Preferably: 0.5-10.0%
　Most Preferably: 1.0-5.0%
Acid/Base Molar Proportions:
　Preferably: 3/1-1/3
　More Preferably: 2/1-1/2
　Most Preferably: 1.25/1-1/1.25

After wall pre-reaction, a water phase is prepared and added carefully to the oil solution. The solutions are milled and heated for a sufficient time to allow wall deposition to proceed. This process is further illustrated and explained in the examples.

In an alternative embodiment, in the first composition, and/or in the anionic emulsifier the initiator can be an energy-activated initiator, relying in place of heat or in addition to heat, on light such as a UV or light induced or electron beam induced free radical. Optionally a visible light induced free radical generator could also be used. This dispersion is then subjected to UV light to generate free radicals and initiate polymerization. Depending on the type of initiator or initiators, the dispersion is subjected to UV light and/or heated (as appropriate to the initiator or initiators) to generate free radicals. The term energy activated is intended to encompass heat, or light, UV or visible or infrared, or electron beam activation, without limitation.

As polymerization progresses, microcapsule wall material forms at the interface of the water and oil phases. UV exposure and/or heating steps can be used to further polymerize or harden the formed wall material.

UV initiators can include ketone compounds and can include benzophenone; acetophenone; benzil; benzaldehyde; o-chlorobenzaldehyde; xanthone; thioxanthone; 9,10-anthraquinone; 1-hydroxycyclohexyl phenyl ketone; 2,2-diethoxyacetophenone; dimethoxyphenylacetophenone; methyl diethanolamine; dimethylaminobenzoate; 2-hydroxy-2-methyl-1-phenylpropane-1-one; 2,2-di-sec-butoxy-acetophenone; 2,2-dimethoxy-1,2-diphenylethan-1-one; dimethoxyketal; and phenyl glyoxal.2,2'-diethoxyacetophenone; hydroxycyclohexyl phenyl ketone; alpha-hydroxyketones; alpha-amino-ketones; alpha and beta naphthyl carbonyl compounds; benzoin ethers such as benzoin methyl ether; benzyl; benzil ketals such as benzil dimethyl ketal; acetophenone, 2-hydroxy-2-methyl-1- phenylpropan-1-one. UV initiators of this kind are available commercially, e.g., IRGACURE 184™ or DEROCURE 1173™ from Ciba. Thermal initiators are available from DuPont. The fraction of the photo initiator in any of the water or oil phase is approximately from about 0.1 to 10%, preferably 0.25 to about 6% by weight, more preferably 0.5 to 2.5 weight percent. Similar weight percent ranges can also be applied to the thermal initiators.

UV initiators can be included in substitution as an alternate initiator system (for any heating step or steps of the encapsulation process, or as an additional initiator system). In a yet further embodiment, for specialized microencapsulation processes, the use of initiators, e.g., thioxanthones, phosphine oxides, metallocenes, tertiary aminobenzenes or tertiary aminobenzophenones, which break down into free radicals on exposure to visible light is effectively used. Such microencapsulation systems however typically require special handling of the system to prevent premature polymerization or oligomerization by appropriate control of lighting conditions.

This produces an initiator system for polymerization or oligomerization using a dual cure method or optional thermal or optional light or optional UV initiated method by appropriate selection of initiator and initiation method or methods. In an alternative embodiment of the invention, azo compounds that can be excited or split by UV light or high-energy radiation are used alone or in combination with thermal free radical initiators. In a yet alternative embodiment, the combination of thermal and UV initiators is formed only by azo compounds.

In a yet further embodiment, for specialized microencapsulation processes, the use of initiators, e.g., thioxanthones, phosphine oxides, metallocenes, tertiary aminobenzenes or tertiary aminobenzophenones, which break down into free radicals on exposure to visible light is effectively used. Such microencapsulation systems however typically require special handling of the system to prevent premature polymerization or oligomerization by appropriate control of lighting conditions.

For light activated microencapsulation, the use of UV initiators are preferred, or a combination of UV initiators and thermal free radical initiators. This combination can impart considerable versatility to the microencapsulation steps of the process where any step or steps of the microencapsulation process then can be initiated either by appropriate selection of an initiator decomposing at specific temperatures or decomposing under specific light conditions. This versatility in the selection of initiators also allows sufficient flexibility in the encapsulation system to customize encapsulation conditions for a given core material. For example, highly volatile or heat-sensitive materials may be more effectively encapsulated with minimal heating, through the use of energy-cure methods.

In a yet further embodiment, with appropriate selection of monomers and initiators, the respective monomers in the process can be polymerized or oligomerized using some suitable means such as heat (used with thermal initiators) or UV light (for use with UV initiators), or electron beam. When replacing the UV radiation with electron beam, the addition of initiators is not absolutely essential or amounts employed can be reduced. Options for individual initiation steps of the encapsulation process include the freedom to use in replacement of any heating step, the use of visible light with suitable initiators, the use of UV light with suitable UV initiators, or ionizing radiation (e.g. electron beam or gamma ray) without initiators or reduced amounts of initiator.

UV initiators may be selected from those organic chemical compounds conventionally employed to promote UV-initiated formation of radicals. A preferred UV initiator is 1-hydroxycyclohexyl phenyl ketone because of the rapidity with which it generates free radicals when exposed to UV radiation. Mixtures of UV initiators or mixtures with thermal initiators may also be used. This is often desirable because it provides more efficient production of radicals in certain cases. In general, the UV initiator will be present in an amount of 0.1 to 10.0 weight percent in any of the water or oil phases, based on the total weight of all constituents. However, it is preferable to use between 0.25-2.5 weight percent UV initiator, most preferably 0.5-1.0 weight percent UV initiator, based on total weight.

The amount of each initiator, thermal, UV or light, that is employed can vary, and is dependent upon factors such as the monomer or oligomer material. Typically, the amount of initiator ranges from about 0.1 to about 6 percent, and often about 1 to about 3 percent, based on the weight of all constituents.

A process of microencapsulation based on UV curing has the advantage of allowing the encapsulation of highly volatile or heat sensitive core materials. UV curable wall systems can have lower energy usage than analogous thermal—cured systems. In certain aspects, a UV-curable system has the potential of increased throughput and efficiency through use of photo initiation.

Various combinations of initiator usage are presented. The first composition can include a thermal initiator or optionally a UV initiator, or both. Similarly the anionic emulsifier of the second composition can include a thermal initiator or optionally a UV initiator, or both. In an alternate aspect of the invention the initiators are UV initiators.

Microcapsule particles according to the invention, by selection of curing conditions, wall materials, initiators, and concentration can select for a desired permeance level allowing formation of capsules with more targeted release profiles appropriate to the end use application. The process of the invention enables manufacture of capsules with different permeability levels. Permeability is conveniently expressed as release of less than a certain quantity of core material over a given time frame. For example, low permeability would be release of less than 1.0 mg/ml at 48 hours extraction time, or less than 2 mg/ml at 1 week extraction time or less than 5 mg/ml at four weeks extraction time. The desired end use application often will dictate the target release rate deemed acceptable to meet the needs of the application.

The examples herein are considered to illustrate the invention and should not be considered as limiting. In all the examples all parts or proportions are by weight and all measurements are in the metric system unless otherwise indicated.

EXAMPLE 1

Preparation of Oil Phases and Pre-Reaction of Wall Material

A first oil phase, consisting of 50 g cedar oil, 0.65 g TBAEMA, and 0.52 g Beta-C, is mixed for about 1 hour before the addition of 26 g CN997. The solution is allowed to mix until needed later in the batch.

A second oil solution consisting of 200 g of cedar oil, 1.56 g Vazo-52 and 0.52 g Vazo-67 is added to a jacketed steel reactor. The reactor is held at 35° C., and the oil solution is mixed at 1000 rpm with a 2" 4-tip flat blade mixer. A nitrogen blanket is applied to the reactor at a rate of 300 cc/min. The solution is heated to 75° C. in 45 minutes and held at 75° C. for 35 minutes, before cooling to 55° C. in 75 minutes. At 55° C., the first oil phase is added, and the combined oils are mixed for another 70 minutes at 55° C.

Water Phase Preparation

A water phase, containing 30g of Colloid 351, 1.1 g 20% NaOH, 600 g water, and 1.56 g Vazo-68WSP, is prepared and mixed until the Vazo is dissolved. The water-phase pH is measured and the solution mixed until needed for batch preparation. The water phase pH for this batch was 4.58.

Capsule Batch Preparation

Once the oil phase temperature has decreased to 55° C., mixing is stopped and the water phase is added to the batch via funnel (to prevent premature mixing of the phases). Mixing is restarted at an appropriate speed to produce an emulsion with the desired size characteristics. In this particular case mixing was done at 3000 rpm for 20 minutes and 2000 rpm for 40 minutes.

When milling was completed, mixing was done with a 3" propeller run at about 400 rpm. The batch was held at 55° C. for another 45 minutes, then the temperature was increased to 75° C. in 30 minutes, held at 75° C. for 4 hours, increased to 90° C. in 30 minutes, and held at 90° C. for 8 hours. The batch was allowed to cool to room temperature at the completion of the heating cycle. The finished batch had a volume-weighted median size of 12.2 µ.

Examples 2 to 23 in Table 1 were similarly prepared. Batch preparation methods are similar to those described in Example 1 with the exceptions stated in Table 1. Water phase pH was adjusted up or down as necessary using either 20% NaOH or concentrated HCl. For examples 5 and 6, milling was continued throughout the batch due to emulsion instability during capsule wall formation. Example 14 and 15 are identical capsules, but for Example 15 the capsule batch pH is adjusted to pH 4. Examples 18 and 19 are similar. In Example 19, the capsule retention study conditions were first adjusted to pH 4. Example 24 is a melamine-formaldehyde wall capsule, shown for comparative purposes.

Capsule Test Data

Capsule test data are shown in Table 1. The table includes capsule leakage data (free-oil, and 4-week hexane leakage), Zeta potential for each batch (a measure of capsule surface charge), and a measure of relative capsule retention.

The abbreviations correspond to the following materials:

|  | Company/City |  |
|---|---|---|
| CN975 | Sartomer Company, Exton, PA | Hexafunctional Aromatic Urethane Acrylate Oligomer |
| CN997 | Sartomer Company, Exton, PA | Hexafunctional Aromatic Urethane Acrylate Oligomer |
| Colloid 121 | Rhone-Poulenc, Cedex, France | Polyacrylic Acid Solution |
| Colloid 351 | Rhone-Poulenc, Cedex, France | Copolymer of 92% Polyacrylic Acid/8% Butyl Acrylate |
| Norpar-12 | Exxon Mobil, Irving, TX | Normal Paraffin Oil |
| Oleocol ME-130 |  | Soybean Oil, Methyl Ester |
| TBAEMA |  | Tertiarybutyl Aminoethyl Methacrylate |
| Vazo-52 | DuPont, Wilmington, DE | 2,2'-Azobis (2,4-Dimethylvaleronitrile) |
| Vazo-67 | DuPont, Wilmington, DE | 2,2'-Azobis (2-Methylbutyronitrile) |
| Vazo-68WSP | DuPont, Wilmington, DE | 4,4'-Azobis (4-Cyanovaleric Acid) |
| Irgacure 651 | CIBA, Tarrytown, NY | 2,2-Dimethoxy-1,2-Diphenylethan-1-one |
| Darocure 1173 | CIBA, Tarrytown, NY | 2-Hydroxy-2-Methyl-1-Phenyl-Propane-1-one |
| Beta-C | Bimax, Glen Rock, PA | Beta-carboxyethyl acrylate |
| Brij-700 | Sigma Aldrick, St. Louis, MO | Polyoxyethylene stearyl ether |
| Celvol 540 PVA | Celanese, Dallas, TX | Polyvinyl alcohol |

Procedure for Determination of Zeta Potential

Supplies needed:
Disposable 10 mL syringes
1 millimolar solution of NaCl/deionized water
Transfer pipets
Syringe filter with 25 mm/30 um filter paper
Malvern Zetasizer, Malvern Instruments Ltd. Model DTS 5300
Rinse Malvern with deionized water by filling a syringe and inserting the tip into the inlet valve. Repeat for a total of 3 rinses with water.
Rinse again, using 1 millimolar solution of NaCL/$H_2O$. Repeat 3 times.
Prepare sample by weighing out 20 g NaCl solution into a disposable beaker. Add 2 drops of capsules (for 20 um size capsules—larger capsules add addition drops). Swirl to mix and draw up a syringe-full. Assemble syringe filter with 30 um paper and filter the capsule solution into another disposable beaker. Using a clean syringe, draw up filtered solution and inject into Malvern.
Record data generated by Malvern Zetasizer
Five readings are made per prepared sample. Rinse instrument between samples.
KCps is:
Mobility is:
Width is:

Procedure for Capsule Retention

Sample Preparation
Substrate Sample: A sample of the substrate for evaluation (typically a fabric), is placed over the inner hoop of an embroidery hoop. The outer hoop is placed over the sample and the inner hoop, the outer hoop is tightened partially, the substrate is pulled tight in the hoop set by pulling the substrate edges, and the outer hoop is fully tightened to securely hold the substrate sample. Excess sample is cut from the edges of the hoop and discarded.

For Table 1, the substrate was cotton fabric, 250 thread count.

Capsule Retention Bath: The capsule retention test is done using a 2000 mL glass beaker as the bath in which the substrate sample is submerged. The beaker is filled to about 1500 mL for all testing. The substrate sample, suspended on an embroidery hoop is placed into the beaker, with the top of the sample just below the liquid level and the bottom of the sample just above a magnetic stir bar that is run to keep movement in the fluid.

Sample Pre-Rinse: A substrate sample is suspended in de-ionized water in the capsule retention bath for 10 minutes to rinse away any fiber fragments, dust, dirt, or water-soluble surface treatments that may exist on the substrate surface. After 10 minutes in the retention bath, the sample is removed and air-dried for 10 minutes.

Microcapsule Retention: Microcapsules are added to a fresh 1500 mL of de-ionized for the microcapsule retention test. The total weight of microcapsules (dry basis) is about 50% of the substrate weight (0.65 g capsules, 1.25 g substrate). The substrate is re-suspended in the retention bath for another 10 minutes. The sample is removed, allowed to dry on the hoop for about 1 hour and is then removed and allowed to air-dry at least 4 hours total.

Extraction Samples: After the retention sample has been air-dried, 2-1" by 3.125" samples are cut from it, using a steel template and razor blade. This provides replicate test samples for the subsequent extraction testing.

Extractions

ISTD (internal standard) Solution: 1 mg/ml Dibutyl Phthalate (DBP)/Hexane (HPLC grade) For 250 ml's: Weigh a little more than 250 mgs of DBP into a small beaker and transfer to a 250 ml volumetric rinsing the beaker thoroughly. Fill to line with hexane.

ISTD Solution: 1 mg/ml Dibutyl Phthalate (DBP)/EtOH (Reagent grade) For 250 ml's: Weigh a little more than 250 mgs of DBP into a small beaker and transfer to a 250 ml volumetric rinsing the beaker thoroughly. Fill to line with EtOH.

Instrumentation:

HP5890 GC connected to HP Chem Station Software

Column: 5 m×0.32 mm id with 1 um DBP-1 liquid phase

Temp: 50 deg for 1 minute then heat to 320 deg @ 15 deg/min

Injector: 275 deg C., Detector: 325 deg C.

2 ul injection

1. Place samples in a 20 ml disposable scintillation vial.
2. Add 15 mL of the Hexane ISTD solution, tightly cap and allow to sit with periodic agitation for 30 minutes standing so the solvent covers the sample.
3. After 30 minutes, transfer a small amount of the Hexane extraction solution to an auto-sampler vial, leaving sample in the vial and allowing it to dry.
4. Add 15 mL of the EtOH ISTD solution to the vials containing the sample and tightly cap.
5. Place the vials in a water bath set at 70° C. for 30 minutes with periodic agitation.
6. After 30 minutes, remove the vials from the water bath and allow them to cool to room temperature, standing so that the solvent covers the sample.
7. Transfer a small amount of the EtOH extraction solution to an auto-sampler vial.

Calculations

For the Standard Solution:

1. Subtract the area count for the internal standard peak from the total area count.

For the Hexane and EtOH extractions:

1. Subtract the area counts for the internal standard peak from the total area counts.
2. Calculate the mg of oil using the following formula $$\frac{\text{Area Count for extraction}}{\text{Area Count for } Std.\ Sol^n} \times Conc.\ \text{Of Oil } Std.\ Sol^n$$

3. Add the mg of oil from the Hexane extraction and EtOH extraction to obtain the total mg of oil.
4. Calculate the % oil released using the following formula $$\frac{\text{mg of Oil from Hexane Extraction}}{\text{Total mg of Oil}} \times 100$$

Preparation of Perfume Oil Standards

Three perfume oil standards should be prepared for GC analysis with the coated sample extractions.

Solution 1

1. Using a disposable Pasteur pipette, weight one (1) drop of the desired perfume oil in a 20 ml disposable scintillation vial.
2. Add 15 mL of the Hexane ISTD solution to the vial, cap and shake vigorously to mix.
3. Record the mg of oil/15 ml.

Example, one drop of perfume oil weighs 14.0 mg. The concentration for this standard solution would be 14 mg/15 ml.
4. Transfer a small amount of the standard solution to an auto-sampler vial and cap for GC analysis.

Solution 2

1. Transfer 5 ml of Standard Solution 1 to a new 20 ml disposable scintillation vial.
2. Add 5 ml of the Hexane ISTD solution to the vial, cap and shake vigorously to mix.
3. Record the mg of oil/15 ml.

Example, the concentration for this standard solution would be 7 mg/15 ml.
4. Transfer a small amount of the standard solution to an auto-sampler vial and cap for GC analysis.

Solution 3

1. Transfer 1 ml of Standard Solution 1 to a new 20 ml disposable scintillation vial.
2. Add 9 ml of the Hexane ISTD solution to the vial, cap and shake vigorously to mix.
3. Record the mg of oil/15 ml.

Example, the concentration for this standard solution would be 1.4 mg/15 ml.
4. Transfer a small amount of the standard solution to an auto-sampler vial and cap for GC analysis.

TABLE 1

| Ex. | Batch | Emulsifer | Emulsifer Level (% of core) | Wall Material | Wall Base | Wall Acid | Water Phase pH | Capsule Size (micron) | Free-Oil (%) | 4-Wk Hexane (mg/ml) | Zeta Potential (mV) | Capsule Retention (mg oil) |
|---|---|---|---|---|---|---|---|---|---|---|---|---|
| 1 | TAS1008081 | Colloid 351 | 3.0 | CN997 | TBAEMA | Beta-C | 4.6 | 12.2 | 0.35 | 7.34 | −57 | 0.3 |
| 2 | TAS1009081 | Celvol 540 PVA | 3.0 | CN997 | TBAEMA | Beta-C | 4.5 | 9.9 | 0.07 | 2.79 | −6 | 2.1 |
| 3 | TAS1010081 | Celvol 540 PVA | 3.0 | CN997 | TBAEMA | HCl | 4.5 | 11.7 | 0.11 | 2.47 | −2 | 2.4 |
| 4 | TAS1013081 | Celvol 540 PVA | 3.0 | CN997 | NaOH | Beta-C | 4.5 | 10.8 | 0.11 | 2.55 | −3 | 1.2 |
| 5 | TAS1030081 | Brij-700 | 3.0 | CN997 | TBAEMA | Beta-C | 4.5 | 25.9 | 14.39 | 9.63 | −4 | 1.2 |
| 6 | TAS1105081 | Dodecyltrimethyl-ammonium Chloride | 3.0 | CN997 | TBAEMA | Beta-C | 4.4 | 13.5 | 9.20 | 16.90 | 13 | 4.0 |
| 7 | TAS1201081 | Poly(ethyleneimine) $M_w$: 750K | 3.0 | CN997 | TBAEMA | Beta-C | 9.4 | 15.9 | 0.07 | 0.45 | 18 | 8.1 |
| 8 | TAS1205082 | Poly(ethyleneimine) $M_w$: 750K | 3.0 | CN997 | TBAEMA | Beta-C | 8.0 | 19.0 | 0.02 | 0.39 | 53 | 8.3 |
| 9 | TAS1208081 | Poly(ethyleneimine) $M_w$: 750K | 3.0 | CN997 | TBAEMA | Beta-C | 11.1 | 22.8 | 0.03 | 0.32 | −4 | 3.4 |
| 10 | TAS1211081 | Poly(ethyleneimine) $M_w$: 750K | 3.0 | CN997 | TBAEMA | HCl | 8.0 | 23.9 | 0.10 | 0.38 | 52 | 7.5 |
| 11 | TAS1215081 | Poly(ethyleneimine) $M_w$: 750K | 3.0 | CN997 | TBAEMA | HCl | 9.5 | 31.9 | 0.13 | 0.40 | 27 | 10.4 |
| 12 | TAS1216081 | Poly(ethyleneimine) $M_w$: 750K | 3.0 | CN997 | TBAEMA | HCl | 6.6 | 29.8 | 1.69 | 0.58 | 41 | 10.5 |
| 13 | TAS1219081 | Poly(ethyleneimine) $M_w$: 750K | 0.6 | CN997 | TBAEMA | HCl | 11.4 | 31.5 | 0.13 | 0.51 | −28 | 5.5 |
| 14 | TAS1230081 | Poly(ethyleneimine) $M_w$: 750K | 3.0 | CN975 | TBAEMA | HCl | 9.8 | 30.1 | 0.06 | | 31 | 12.6 |
| 15 | TAS1230081 (B) | Poly(ethyleneimine) $M_w$: 750K | 3.0 | CN975 | TBAEMA | HCl | 9.8 (4.0) | 30.1 | 0.09 | | 51 | 7.1 |
| 16 | TAS0106091 | Poly(ethyleneimine) $M_w$: 25K | 3.0 | CN975 | TBAEMA | HCl | 10.0 | 22.2 | 0.01 | 0.29 | 18 | 8.2 |
| 17 | TAS0107091 | Poly(ethyleneimine) $M_w$: 25K | 3.0 | CN975 | NaOH | Beta-C | 10.0 | 22.8 | 0.01 | 0.31 | 12 | 6.4 |
| 18 | TAS0112091 | Poly(ethyleneimine) $M_w$: 25K | 3.0 | CN975 | TBAEMA | HCl | 8.5 | 19.3 | 0.01 | | 65 | 8.0 |
| 19 | TAS0112091 (B) | Poly(ethyleneimine) $M_w$: 25K | 3.0 | CN975 | TBAEMA | HCl | 8.5 (3.0) | 19.3 | 0.01 | 0.40 | n/a | 4.4 |
| 20 | TAS0113091 | Poly(ethyleneimine) $M_w$: 25K | 3.0 | CN975 | NaOH | Beta-C | 8.5 | 23.2 | 0.01 | 0.38 | 59 | 12.1 |
| 21 | TAS0115091 | Poly(ethyleneimine) $M_w$: 25K | 3.0 | CN975 | TBAEMA | Beta-C | 10.0 | 15.8 | 0.02 | | 22 | 5.0 |
| 22 | TAS0116091 | Poly(ethyleneimine) $M_w$: 25K | 3.0 | CN975 | TBAEMA | Beta-C | 8.5 | 23.8 | 0.02 | | 63 | 7.4 |
| 23 | TAS0120091 | Poly(ethyleneimine) $M_w$: 2K | 3.0 | CN975 | NaOH | Beta-C | 10.1 | 32.3 | 0.03 | | −3 | 4.5 |
| 24 | PS020309 | Colloid 351 | | Melamine | n/a | n/a | | 15.1 | | | −57 | 0.6 |

In Table 1 capsule retention on cotton fiber is usefully at least 1 mg oil determined following the capsule retention procedure set forth herein. The invention makes possible capsule retention values of at least 1 mg oil, or even at least 4 mg oil, or even at least 8 mg oil, or even at least 10 mg oil.

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive variations and changes can be made by those skilled in the art without departing from the spirit and scope of the invention.

What is claimed is:

1. A population of microcapsule particles comprising an oil soluble or dispersible core material and a non-anionic wall material at least partially surrounding the core material, the microcapsule wall material consisting of:

the reaction product of a first composition in the presence of a second composition consisting of an emulsifier which is non-anionic, the first composition consisting of a reaction product of i) an oil soluble or dispersible amine acrylate or methacrylate with ii) a multifunctional acrylate or methacrylate monomer or oligomer, and iii) a soluble acid and an initiator, wherein the ratio of amine acrylate or methacrylate to multifunctional acrylate or methacrylate is from 0.1:99.9 to 10:90 by weight, wherein the soluble acid and the amine acrylate are in a molar proportion from 3:1 to 1:3 and together have a percent by weight as compared to the weight of the wall material of from 0.1 to 20%, the non-anionic emulsifier comprising a water soluble or dispersible material at a pH from 4 to 12, and optionally a water phase initiator, whereby the reaction product of the first composition and second composition results in the formation of a population of microcapsules having a non-anionic microcapsule wall material of low permeance to the core material and having a zeta potential of −5 millivolts or greater, the resulting microcapsules having adherence to anionic surfaces.

2. The population of microcapsule particles according to claim 1 wherein the emulsifier is cationic.

3. The population of microcapsules according to claim 2 wherein the cationic emulsifier is selected from palmitamidopropyltrimonium chloride, distearyl dimonium chloride, cetyltrimethylammonium chloride, quaternary ammonium compounds, fatty amines, aliphatic ammonium halides, alkyldimethylbenzylammonium halides, alkyldimethylethylammonium halides, polyethyleneimine, poly(2-dimethylamino) ethyl methacrylate)methyl chloride quaternary salt, poly(1-vinylpyrrolidone-co-2-dimethylaminoethyl methacrylate), poly(acrylamide-co -diallyldimethylammonium chloride), poly(allylamine), poly[bis(2-chloroethyl)ether-alt-1,3-bis[3-(dimethylamino)propyl]urea] quaternized, poly(dimethylamine-co-epichlorohydrin-co-ethylenediamine) and condensation products of aliphatic amines with alkylene oxide.

4. The population of microcapsules according to claim 3 wherein the soluble acid and amine acrylate have a percent by weight as compared to the weight of the wall material of from 1 to 5 percent.

5. The population of microcapsules according to claim 3 wherein the soluble acid and amine acrylate have a molar proportion of from 1.25/1 to 1/1.25.

6. The population of microcapsules according to claim 1 wherein the non-anionic emulsifier comprises a water soluble or dispersible material at a pH of from 8-10.

7. The population of microcapsule particles according to claim 1 wherein the emulsifier is nonionic.

8. The population of microcapsules according to claim 7 wherein the nonionic emulsifier is selected from polyalkylene glycol ether, condensation products of alkyl phenols, aliphatic alcohols, or fatty acids with alkylene oxide, ethoxylated alkyl phenols, ethoxylated arylphenols, ethoxylated polyaryl phenols, carboxylic esters solubilized with a polyol, polyvinyl alcohol, partially hydrolyzed polyvinyl alcohol, polyvinyl acetate, copolymers of polyvinyl alcohol, copolymers of polyvinyl acetate, polyacrylamide, poly(N-isopropylacrylamide), poly(2-hydroxypropyl methacrylate), poly(2-ethyl-2-oxazoline), poly(2-isopropenyl-2-oxazoline-co-methyl methacrylate), poly(methyl vinyl ether), and polyvinyl alcohol-co-ethylene).

9. The population of microcapsules according to claim 8 wherein the soluble acid and amine acrylate have a percent by weight as compared to the weight of the wall material of from 1 to 5 percent.

10. The population of microcapsules according to claim 8 wherein the soluble acid and amine acrylate have a molar proportion of from 1.25/1 to 1/1.25.

11. The population of microcapsules according to claim 1 wherein the emulsifier has a molecular weight greater than about 100, and is selected from polymers with primary, secondary or tertiary amine functionality.

12. The population of microcapsules according to claim 1 wherein the emulsifier has a molecular weight greater than 100 and is selected from polymers with hydroxyl, ether, ester, ketone or amide functionality.

13. A population of microcapsule particles comprising an oil soluble or dispersible core material and a non-anionic wall material at least partially surrounding the core material, the microcapsule wall material consisting of:
   the reaction product of a first composition in the presence of a second composition consisting of an emulsifier which is non-anionic, the first composition consisting of a reaction product of i) an oil soluble or dispersible acid acrylate or methacrylate with ii) a multifunctional acrylate or methacrylate monomer or oligomer, and iii) a soluble base and an initiator,
   wherein the ratio of amine acrylate or methacrylate to multifunctional acrylate or methacrylate is from 0.1:99.9 to 10:90 by weight,
   wherein the soluble base and the acid acrylate are in a molar proportion from 3:1 to 1:3 and together have a percent by weight as compared to the weight of the wall material of from 0.1 to 20%,
   the non-anionic emulsifier comprising a water soluble or dispersible material at a pH from 4 to 12, and optionally a water phase initiator,
   whereby the reaction product of the first composition and second composition results in the formation of a population of microcapsules having a non-anionic microcapsule wall of low permeance to the core material and having a zeta potential of −5 millivolts or greater, the resulting microcapsules having adherence to anionic surfaces.

14. The population of microcapsule particles according to claim 13 wherein the emulsifier is cationic.

15. The population of microcapsules according to claim 14 wherein the cationic emulsifier is selected from palmitamidopropyltrimonium chloride, distearyl dimonium chloride, cetyltrimethylammonium chloride, quaternary ammonium compounds, fatty amines, aliphatic ammonium halides, alkyldimethylbenzylammonium halides, alkyldimethylethylammonium halides, polyethyleneimine, poly(2-dimethylamino) ethyl methacrylate)methyl chloride quaternary salt, poly(1-vinylpyrrolidone-co-2-dimethylaminoethyl methacrylate), poly(acrylamide-co-diallyldimethylammonium chloride), poly(allylamine), poly[bis(2-chloroethyl)ether-alt-1,3-bis[3-(dimethylamino)propyl]urea] quaternized, poly(dimethylamine-co-epichlorohydrin-co-ethylenediamine) and condensation products of aliphatic amines with alkylene oxide.

16. The population of microcapsules according to claim 15 wherein the soluble acid and amine acrylate have a percent by weight as compared to the weight of the wall material of from 1 to 5 percent.

17. The population of microcapsules according to claim 15 wherein the soluble acid and amine acrylate have a molar proportion of from 1.25/1 to 1/1.25.

18. The population of microcapsules according to claim 15 wherein the non-anionic emulsifier comprises a water soluble or dispersible material at a pH of from 8-10.

19. The population of microcapsule particles according to claim 13 wherein the emulsifier is nonionic.

20. The population of microcapsules according to claim 19 wherein the nonionic emulsifier is selected from polyalkylene glycol ether, condensation products of alkyl phenols, aliphatic alcohols, or fatty acids with alkylene oxide, ethoxylated alkyl phenols, ethoxylated arylphenols, ethoxylated polyaryl phenols, carboxylic esters solubilized with a polyol, polyvinyl alcohol, polyvinyl acetate, copolymers of polyvinyl alcohol, copolymers of polyvinyl acetate, polyacrylamide, poly(N-isopropylacrylamide), poly(2-hydroxypropyl methacrylate), poly(2-ethyl-2-oxazoline), poly(2-isopropenyl-2-oxazoline-co-methyl methacrylate), poly(methyl vinyl ether), and polyvinyl alcohol-co-ethylene).

21. The population of microcapsules according to claim 20 wherein the soluble acid and amine acrylate have a percent by weight as compared to the weight of the wall material of from 1 to 5 percent.

22. The population of microcapsules according to claim 20 wherein the soluble acid and amine acrylate have a molar proportion of from 1.25/1 to 1/1.25.

23. The population of microcapsules according to claim 13 wherein the emulsifier has a molecular weight greater than about 100, and is selected from polymers with primary, secondary or tertiary amine functionality.

24. The population of microcapsules according to claim 13 wherein the emulsifier has a molecular weight greater than 100 and is selected from polymers with hydroxyl, ether, ester, ketone or amide functionality.

25. The population of microcapsules according to claim 20 wherein the nonionic emulsifier is partially hydrolyzed polyvinyl alcohol in the range of from 85 to 95% hydrolyzed.

* * * * *